United States Patent
Haras et al.

(10) Patent No.: US 7,822,170 B2
(45) Date of Patent: Oct. 26, 2010

(54) METHOD, TOMOGRAPHY SYSTEM AND IMAGE PROCESSING SYSTEM FOR DISPLAYING TOMOGRAPHIC RECORDS OF A PATIENT

(75) Inventors: Gabriel Haras, Mücke (DE); Peter Aulbach, Forchheim-Kersbach (DE); Dieter Böing, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 230 days.

(21) Appl. No.: 12/153,484

(22) Filed: May 20, 2008

(65) Prior Publication Data
US 2008/0292048 A1 Nov. 27, 2008

(30) Foreign Application Priority Data
May 25, 2007 (DE) .................. 10 2007 024 452

(51) Int. Cl.
*A61B 6/03* (2006.01)
(52) U.S. Cl. .................. 378/8; 250/363.04; 324/307
(58) Field of Classification Search .................. 378/4, 378/8, 19, 20; 250/363.04; 324/307
See application file for complete search history.

(56) References Cited

U.S. PATENT DOCUMENTS

2006/0056674 A1  3/2006  Lehtonen-Krause

2007/0012880 A1  1/2007  Haider et al.
2007/0019781 A1  1/2007  Haras

FOREIGN PATENT DOCUMENTS

| DE | 10 2004 043 263 | 3/2006 |
| DE | 10 2005 029 242 | 12/2006 |
| DE | 10 2005 034 684 | 2/2007 |

OTHER PUBLICATIONS

German Office Action issued Mar. 7, 2008.

*Primary Examiner*—Chih-Cheng G Kao
(74) *Attorney, Agent, or Firm*—Harness, Dickey & Pierce, P.L.C.

(57) ABSTRACT

A method and a tomographic system are disclosed for displaying tomographic records of a patient. In at least one embodiment, the method includes scanning the patient with the aid of a tomographic system having one system axis, determining at least one topogram, calculating three-dimensional image data records including a multiplicity of slice images on a plane or volume data records, and outputting at least one slice image of the patient. In at least one embodiment, the orientation of individual body zones relative to the system axis of the tomographic system is automatically determined from the at least one topogram, and slice images of the body zones are calculated from the three-dimensional image data records, the slice planes of which are at a defined solid angle to the previously determined orientation of the scanned body zones.

26 Claims, 3 Drawing Sheets

US 7,822,170 B2

METHOD, TOMOGRAPHY SYSTEM AND IMAGE PROCESSING SYSTEM FOR DISPLAYING TOMOGRAPHIC RECORDS OF A PATIENT

PRIORITY STATEMENT

The present application hereby claims priority under 35 U.S.C. §119 on German patent application number DE 10 2007 024 452.7 filed May 25, 2007, the entire contents of which is hereby incorporated herein by reference.

FIELD

Embodiments of the invention generally relate to a method for displaying tomographic records of a patient, in particular with the aid of a CT, PET or NMR system, or tomographic systems combined therefrom, with a scan of the patient being carried out with the aid of a tomographic system having one system axis, at least one topogram being determined and a calculation of three-dimensional image data records comprising a multiplicity of slice images on one plane or volume data records being carried out and with at least one slice image of the patient being output.

Furthermore, embodiments of the invention generally relate to a system for generating and displaying tomographic slice image records of a patient, in particular comprising a CT, PET or NMR recording system or a recording system combined therefrom, having at least one calculating and display unit with at least one memory, in which program code for imaging based on tomographic image data records is saved and furthermore an image processing system for displaying tomographic slice image records of a patient on the basis of tomographic data, in particular from a CT, PET or NMR recording system or a recording system combined therefrom, having at least one calculating and display unit with at least one memory, in which program code for imaging based on tomographic image data records is saved.

BACKGROUND

Method for displaying tomographic records of a patient and the corresponding CT systems and image processing systems are generally known. In almost every tomographic system, tomographic records are computed, with the correct scanning region often also being determined in advance with the aid of a tomogram, and subsequently three-dimensional image data records comprising a multiplicity of slice images on one plane or volume data records being calculated and slice images of the patient being output to be examined by the operator or for later diagnostic purposes. In order to generate such records, the patient is generally laid on a patient couch and aligned as far as possible with the system axis of the respective tomographic system in order to obtain images which change as little as possible in different scans.

The problem is that not all patients stay in an optimum still position, but some move in the time between being arranged by the staff and the actual recording, and are scanned in a different position. In general, slice images are now calculated on an axial plane, which is perpendicular to the system axis, and also output on this slice plane.

If the patient is not optimally placed, slice images are created which are difficult to interpret due to their spatial orientation relative to the patient or to individual body parts of the patient. For this reason, it is sometimes necessary to manually redefine the slice planes, the orientation of which is used to output new slice images based on already scanned three-dimensional image data records, in order to allow a better diagnostic evaluation.

Such a method with manual inputs to correct the slice image planes of the slice images output is very complex and is very often subject to subjective decisions by the staff, so that there is a relatively wide bandwidth with regard to the later output slice planes, which can lead to problems in particular when comparing equivalent representations at different times in the patient's history.

SUMMARY

In at least one embodiment of the invention, a method is disclosed which allows an improved capability to diagnose the records and an improved capability to compare slice image records of a patient taken at different times. It is likewise an object of the invention to describe a corresponding tomographic system and an image processing system to carry out this method.

The inventors have recognized that, using a previously carried out automatic recognition of the orientation of the patient or the orientation of body parts of the patient relative to the system axis of the recording system, it is possible to ensure with the aid of a coordinate transformation that the slice images of the patient or body parts of the patient are always displayed with the same orientation relative to the main orientation axis of the respective body part or the entire patient.

Based on this discovery, the inventors propose a method for, in at least one embodiment, displaying tomographic records of a patient, in particular with the aid of a CT, PET or NMR system or tomographic systems combined therefrom, comprising the following method steps:
  scanning the patient with the aid of a tomographic system having one system axis,
  determining at least one topogram,
  calculating three-dimensional image data records comprising a multiplicity of slice images on one plane or volume data records,
  outputting at least one slice image of the patient.

According to at least one embodiment of the invention, this method mentioned above is improved by the orientation of individual body zones, that is to say individual body regions and/or body parts and/or extremities, relative to the system axis of the tomographic system being determined automatically from the at least one topogram, and by slice images of the body zones being calculated from the three-dimensional image data records, the slice planes of which are at a defined solid angle to the previously determined orientation of the scanned body zones.

Hence, the orientation of individual body zones is now determined with the aid of a previously determined topogram and these body zones are effectively normalized with respect to the direction of the slice images for the slice images to be produced later, so that slice images of the respective body zones, always oriented in the same way, are displaced relative to the orientation of the body zones, independently of the positioning of the patient relative to the system axis. This achieves an optimum ability to compare and diagnose these images, in which case, even images created at different times can be optimally compared with each other.

One particular embodiment of this method proposes that the patient is placed on a patient couch which largely determines the orientation of the body zones on at least one plane and that the orientation of the body zones be determined using the knowledge of this at least one predefined plane and a single topogram. Thus, should the situation arise, this means that it is sufficient to correct the orientation correction on only one plane, namely on that plane corresponding to the resting plane of the patient in the respective body zone on the patient couch. Generally this is a single plane; however, in special cases a patient couch can be used which has a differing orientation depending on the body zone, so that this differing orientation depending on the body zone has to be considered as well.

A further advantageous embodiment includes two or more topograms, oriented at an angle to another, being generated. As a result of this it is possible to determine the orientation of the body zones solely from the at least two topograms without making use of further position information.

It is furthermore proposed that that at least one topogram be recorded by a separate pre-scan or that one topogram be generated during the actual scan, in which case it is also possible to directly generate a plurality of topograms from different directions during the scan.

However, it is also possible to generate a topogram computationally by evaluating the three-dimensional image data records.

Moreover, at least one topogram can be created with the aid of other physical methods as the actual three-dimensional scan of the patient. By way of example, this means that it is possible to create the topogram with the aid of x-rays, while the actual scan is carried out with the aid of magnetic resonance or PET measurements.

By way of example, the entire patient or individual extremities or their partial zones connected by joints can be used as the body zone whose orientation is determined. It is also possible to consider the torso or the neck to be the body zone, and curvature of the spine can be taken into account, as a result of which the orientation of the respective body zone relative to the system axis can vary along its profile, which can likewise be taken into account during the creation of slice images.

Finally, it is also possible to consider the head as the body zone and determine its position.

Corresponding to the method in at least one embodiment described above, a tomographic system, for example a CT system, a PET system, an NMR system or a tomographic system combined from the abovementioned systems, can also be equipped with program code which executes the previously described method during its operation.

If the required three-dimensional image data records and, if applicable, finished topograms as well are transferred to an image processing system, the methods described above can likewise be carried out on an image processing system once it has corresponding program code in its memory, which is executed during its operation.

BRIEF DESCRIPTION OF THE DRAWINGS

In the following text, embodiments of the invention are described in more detail with aid of the figures, with only the features required to understand the invention being illustrated. In this case, the following reference symbols are used: 1—CT system; 2—first x-ray tube; 3—first detector system; 4—second x-ray tube; 5—second detector system; 6—gantry housing; 7—patient; 7.1—head; 7.2—neck region; 7.3—right arm; 7.4—left arm; 7.5—torso; 7.6—right leg; 7.7—left leg; 8—patient couch; 9—control and calculating unit; 10—memory of the control and calculating unit; 11.1—display area head; 11.2—display area neck; 11.3—display area right arm; 11.4—display area left arm; 11.5—display area torso; 11.6—display area right leg; 11.7—display area left leg; 12.1-12.7—reconstruction zone; 13.1—coronal plane; 13.2—sagittal plane; 13.3—axial plane; $Prg_1$ to $Prg_n$—computer programs; x, y, z—coordinates of the tomographic system; x', y', z'—patient coordinates or coordinates of the body zones; Z—system axis.

In detail.

DETAILED DESCRIPTION OF THE EXAMPLE EMBODIMENTS

Figure 1:
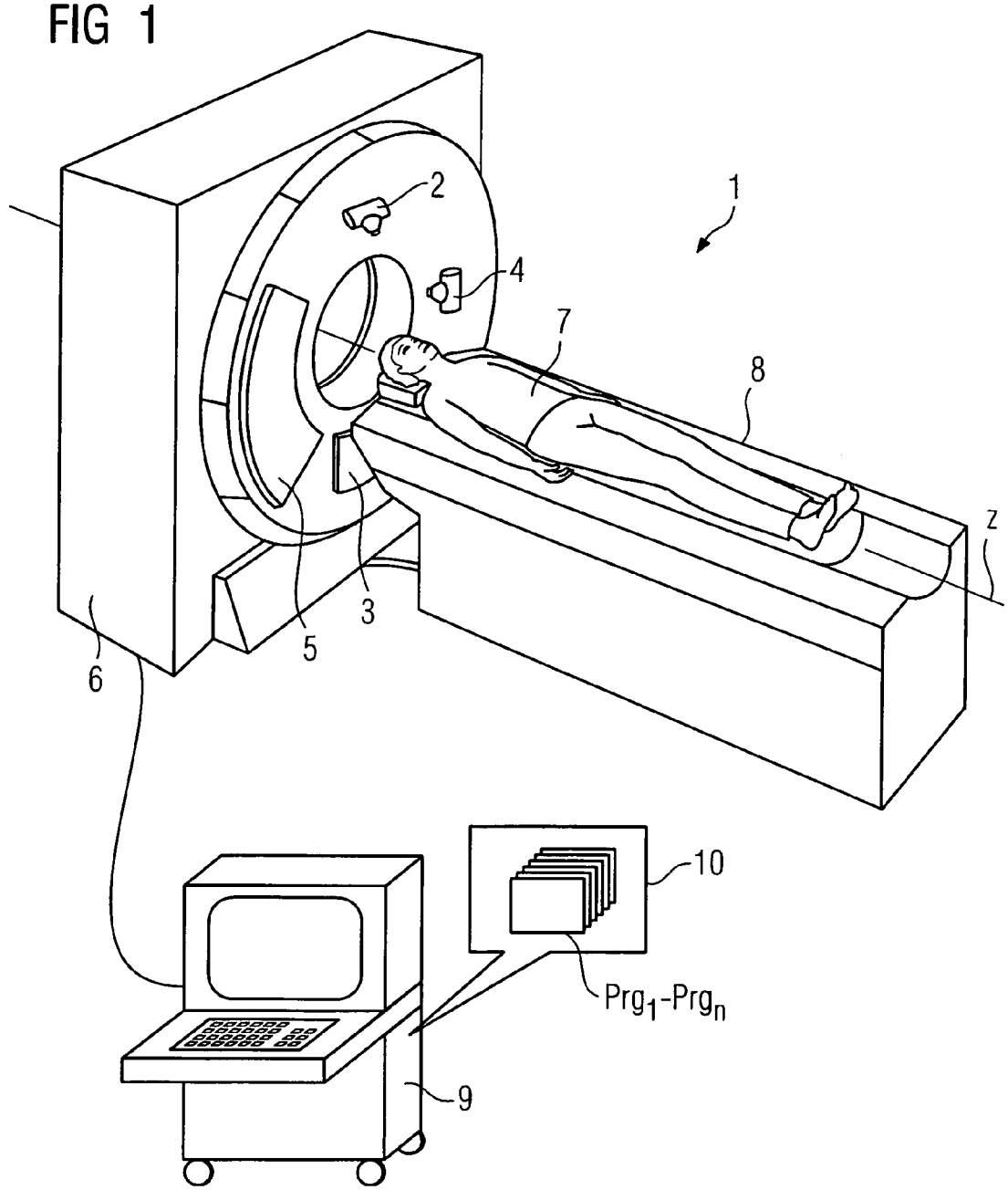
FIG. 1 shows a CT system.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

By way of example, FIG. 1 shows a CT system 1, which is representative of all the previously mentioned tomographic systems. The CT system 1 includes two focus detector systems in the gantry housing 6, the detector systems comprising a first x-ray tube 2, a first detector 3 lying opposite and a second x-ray tube 4 arranged offset at an angle and with an opposite second detector 5. A patient 7 is situated on the patient couch, and can be pushed into the scanning region of the CT system along the system or z-axis of the CT system 1. The control of the CT system and evaluation of the detector data with reconstruction of the tomographic data and, if applicable, the creation of a topogram as well are carried out by the control and calculating unit 9. For this purpose, computer programs $Prg_1$ to $Prg_n$ which carry out the corresponding methods during operation are saved in the memory 10 of the calculating unit 9. Some of these computer programs are also programs which carry out at least one embodiment of the inventive method for displaying tomographic records.

When placing a patient 7 on the couch, the problem that the alignment of the patient cannot be carried out optimally or that the patient moves between being placed on the couch and the subsequent scan occurs repeatedly, so that the slice images on the scanning plane normally created by the system are not necessarily useful for later diagnosis since their orientation may substantially differ from the orientation of the scanned body zones.

Figure 2:
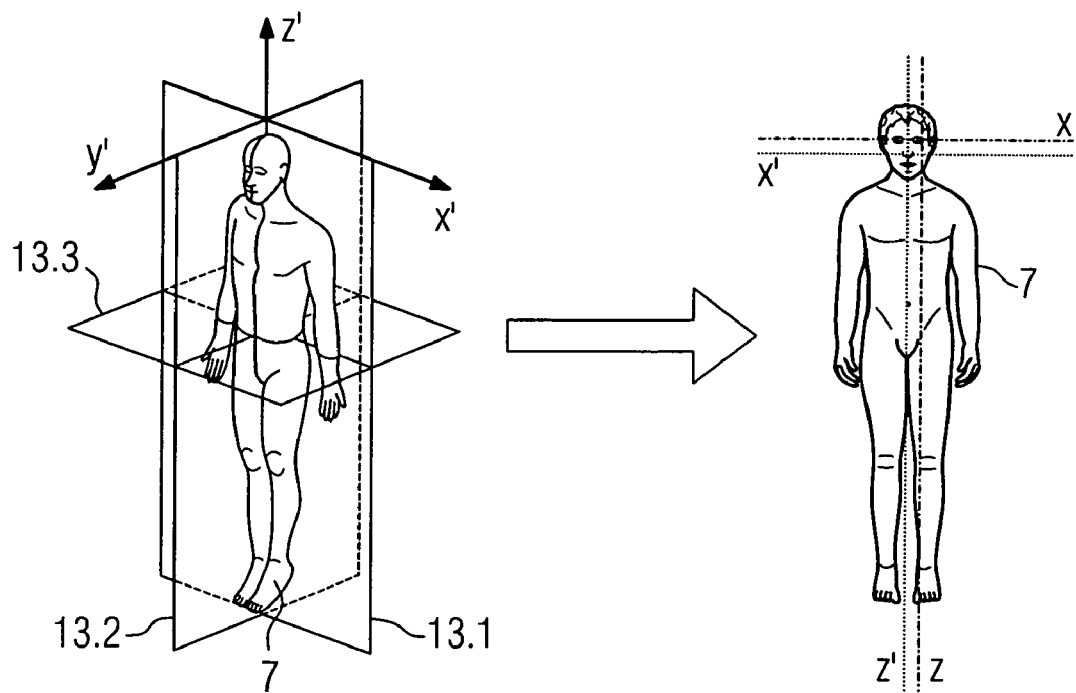
FIG. 2 shows slice planes of a patient and coordinate system of the patient in the tomographic system.

FIG. 2 shows the medical definition of the slice planes of a patient 7 with the patient-specific axes x', y' and z'. The plane defined by the x' and z' axes corresponds to the coronal slice plane 13.1. The plane defined by the z' and y' axes corresponds to the sagittal slice plane 13.2 and the plane defined by the two x' and y' planes corresponds to the axial slice plane 13.3. If the patient, with his major axes x' and z', is correctly placed on the patient couch of a tomographic system, as illustrated on the right-hand side of FIG. 2, then the patient's major axes x' and z' correspond to the system's major axes x and z.

Figure 3:
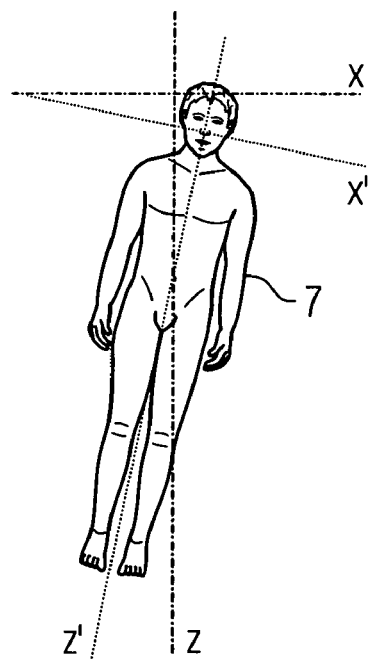
FIG. 3 shows a patient arranged at an angle in the coordinate system of the tomographic system.

A problem arises when, as illustrated in FIG. 3, a patient is, either as a whole or partially, placed at an angle to the axes of the tomographic system, so that, as can be seen here, the z' axis of the patient 7 is no longer oriented with the z axis of the tomographic system and, possibly, the x' axis of the patient is also no longer oriented parallel to the x axis of the tomographic system. Consequently, the axial slices related to the system axis of the tomographic system will no longer correspond to the patient related axial slices. According to an embodiment of the invention, the orientation of the patient is now automatically determined with the aid of one or more recorded topograms, or the orientation of individual body zones of the patient is determined and the displayed slices, corresponding to this orientation of the patient, are corrected, so that slice images are shown which are always aligned with the patient axis or the orientation of the individual body parts of the patient.

Figure 4:
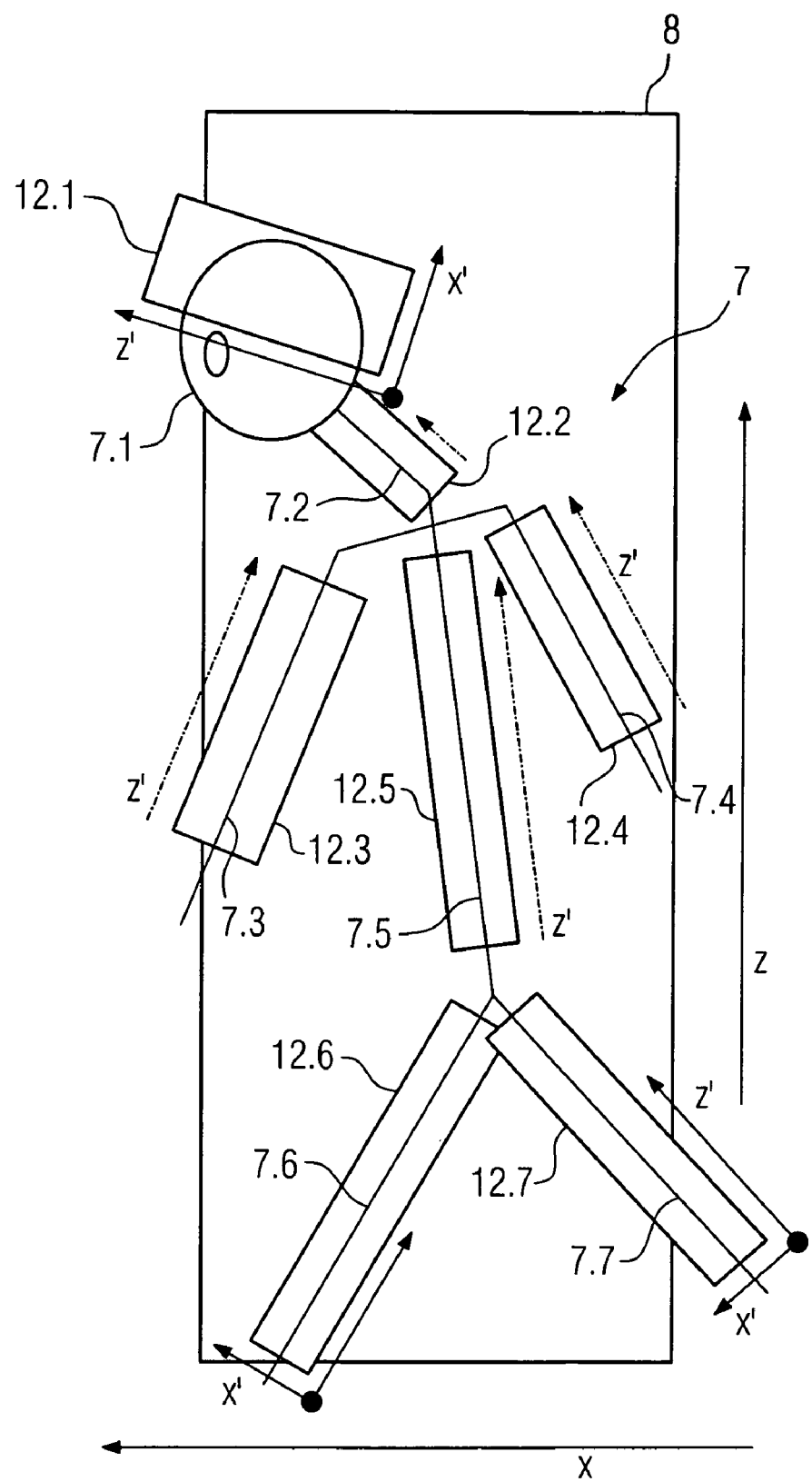
FIG. 4 shows an illustration of the different body zones displaced with respect to the coordinate system of the tomographic system.

While FIG. 3 shows a patient 7 whose entire body axis is twisted with respect to the system axis of the tomographic system, FIG. 4 shows an illustration of a patient 7 which, albeit slightly exaggerated, corresponds more to reality; the patient being placed on a couch 8 with all his extremities and torso, including head and neck, being twisted with respect to the actual system axes of the tomographic system. The patient 7 is shown here in the form of a "stick figure" with a head 7.1, a neck 7.2, the right and left arm 7.3 and 7.4, a torso 7.5 and the right and left leg 7.6 and 7.7. Parallel to these body zones 7.1 to 7.7, the orientation axes of these body zones z' and x' are shown, none of which are parallel to the alignments of the system axes of the tomographic system z and x.

According to an embodiment of the invention, these individual alignments of the body zones 7.1 to 7.7 are now automatically recognized by a calculating system by way of one or more recorded topograms, with the aid of a pattern recognition method for example, and the illustrated slice planes of the corresponding reconstruction zones 12.1 to 12.7 are then displayed orthogonal to the patient related coordinate system z' and x'. Due to this display of the tomographic record respectively oriented to the patient coordinate system, this results in better diagnosis for this record, and records obtained at different times can be compared in an improved manner. In contrast to manual evaluations, an embodiment of this method additionally has the advantage that individual errors in the alignment of the images to be shown are avoided and differences that can occur from operator to operator likewise no longer occur. Furthermore, this method results in effective saving of time compared to the manual alignment of slice images on the basis of patient related coordinate systems.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

It is self-evident that the features of embodiments of the invention mentioned above can be used not only in the respectively stated combination, but also in other combinations or on their own, without departing from the scope of the invention.

What is claimed is:

1. A method for displaying tomographic records of a patient, comprising:
   scanning the patient with the aid of a tomographic system having a system axis;
   determining at least one topogram;
   automatically determining orientation of scanned body zones of the patient, relative to the system axis of the tomographic system, from the at least one topogram;
   calculating three-dimensional image data records including a multiplicity of slice images of the body zones, slice planes of the slice images being at a defined solid angle to the determined orientation of the scanned body zones; and
   outputting at least one slice image of the patient.

2. The method as claimed in claim 1, wherein the patient is placed on a patient couch which largely determines the orientation of the body zones on at least one plane and wherein the orientation of the body zones is determined using the knowledge of this at least one plane and a single topogram.

3. The method as claimed in claim 2, wherein two or more topograms, oriented at an angle to another, are generated.

4. The method as claimed in claim 1, wherein two or more topograms, oriented at an angle to another, are generated.

5. The method as claimed in claim 4, wherein at least one topogram is recorded by a pre-scan.

6. The method as claimed in claim 4, wherein at least one topogram is generated during an actual scan.

7. The method as claimed in claim 4, wherein at least one topogram is generated computationally by evaluation of the three-dimensional image data records.

8. The method as claimed in claim 4, wherein at least one topogram is generated by a different physical method than the three-dimensional scan of the patient.

9. The method as claimed in claim 1, wherein at least one topogram is recorded by a pre-scan.

10. The method as claimed in claim 1, wherein at least one topogram is generated during an actual scan.

11. The method as claimed in claim 1, wherein at least one topogram is generated computationally by evaluation of the three-dimensional image data records.

12. The method as claimed in claim 1, wherein at least one topogram is generated by a different physical method than the three-dimensional scan of the patient.

13. The method as claimed in claim 1, wherein the whole patient is used as the body zone whose orientation is determined.

14. The method as claimed in claim 1, wherein individual extremities of the patient, or their partial zones connected by joints, are used as the body zones whose orientation is determined.

15. The method as claimed in claim 1, wherein a torso of the patient is used as the body zone whose orientation is determined.

16. The method as claimed in claim 15, wherein curvature of the spine of the patient is taken into account, as a result of which the orientation changes along a profile of the spine.

17. The method as claimed in claim 1, wherein a neck of the patient is used as the body zone whose orientation is determined.

18. The method as claimed in claim 17, wherein curvature of the spine of the patient is taken into account, as a result of which the orientation changes along the profile of the spine.

19. The method as claimed in claim 1, wherein a head of the patient is used as the body zone whose orientation is determined.

20. A system for generating and displaying tomographic slice image records of a patient, comprising:
    at least one calculation and control unit including at least one memory in which program code for imaging based on tomographic image data records is saved, the program code, when executed during operation of the at least one calculation and control unit, is adapted to perform the method of claim 1.

21. The system of claim 20, further comprising a CT, PET, NMR recording system or a recording system combined therefrom.

22. An image processing system for displaying tomographic slice image records of a patient based on tomographic data, comprising:
    at least one calculation and control unit including at least one memory in which program code for imaging based on tomographic image data records is saved, the program code, when executed during operation of the at least one calculation and control unit, is adapted to perform the method of claim 1.

23. The image processing system of claim 22, further comprising a CT, PET, NMR recording system or a recording system combined therefrom.

24. The method of claim 1, wherein the method is for displaying tomographic records of a patient with the aid of a CT, PET or NMR system, or tomographic systems combined therefrom.

25. The method of claim 1, wherein in the automatically determining, the scanned body zones of the patient include at least one of body regions, body parts and extremities.

26. A system for displaying tomographic records of a patient, comprising:
    means for scanning the patient with the aid of a tomographic system having a system axis;
    means for determining at least one topogram;

means for automatically determining orientation of scanned body zones of the patient, relative to the system axis of the tomographic system, from the at least one topogram;

means for calculating three-dimensional image data records including a multiplicity of slice images of the body zones, slice planes of the slice images being at a defined solid angle to the determined orientation of the scanned body zones; and means for outputting at least one slice image of the patient.

* * * * *